United States Patent [19]
Uchida

[11] Patent Number: 6,145,990
[45] Date of Patent: Nov. 14, 2000

[54] AUTOMATIC ALIGNMENT OPTOMETRIC MEASUREMENT APPARATUS AND METHOD USING THE SAME

[75] Inventor: Koji Uchida, Utsunomiya, Japan

[73] Assignee: Canon Kabushiki Kaisha, Tokyo, Japan

[21] Appl. No.: 09/352,200

[22] Filed: Jul. 13, 1999

[30] Foreign Application Priority Data

Jul. 16, 1998 [JP] Japan .................................. 10-219697

[51] Int. Cl.[7] ...................................................... A61B 3/10
[52] U.S. Cl. ............................................................ 351/221
[58] Field of Search .................................. 351/205, 206, 351/208, 211, 212, 221

[56] References Cited

U.S. PATENT DOCUMENTS 4,715,703  12/1987  Cornsweet ............................... 351/205
5,781,275  7/1998  Kohayakawa ............................. 351/205

*Primary Examiner*—George Manuel
*Attorney, Agent, or Firm*—Fitzpatrick, Cella, Harper & Scinto

[57] ABSTRACT

An optometric apparatus includes a luminous flux projecting unit for projecting a luminous flux to one eye of a subject to be measured, an imaging unit for imaging an anterior part of the eye illuminated by the luminous flux projecting unit, a position detecting unit for detecting the position of the eye in accordance with an image output from the imaging unit, an optometric unit for measuring the eye, a drive unit for driving the optometric unit, and a control unit for controlling the drive unit. The control unit controls the drive unit to align the optometric unit with the eye in accordance with a signal output from the position detecting unit and then controls the drive unit to move the optometric unit to the other eye of the subject when the measurement of the one eye by the optometric unit is completed.

16 Claims, 14 Drawing Sheets

F I G. 10
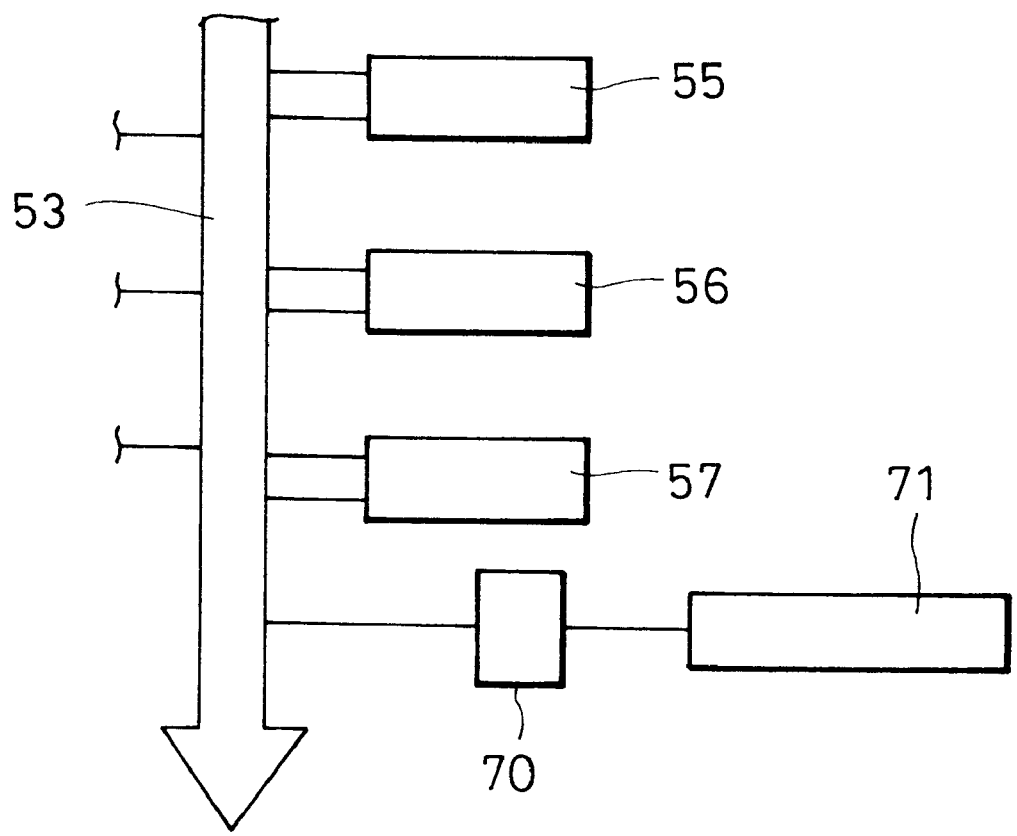

AUTOMATIC ALIGNMENT OPTOMETRIC MEASUREMENT APPARATUS AND METHOD USING THE SAME

BACKGROUND OF THE INVENTION

1. Field of the Invention

The present invention relates to an optometric apparatus and an optometric measurement method that automatically aligns with an eye to be measured, by driving a drive means in accordance with position information from a position detecting means.

2. Description of the Related Art

Known optometric apparatuses include position detecting means for detecting the position of an eye to be measured, and drive means for moving the apparatus in any direction, upward or downward, rightward or leftward, and forward or backward. Such an optometric apparatus automatically aligns with the eye of a subject by driving the drive means in accordance with position information from the position detecting means. When an operator presses a measurement switch, the apparatus measures a relative position of the eye to be measured and the apparatus, and part of the apparatus moves so that the apparatus aligns with the position of the eye to be measured. When a positional error between the eye and the apparatus falls within a predetermined permissible range, an optometric measurement is initiated.

When the measurement of the one eye is completed, an optometric unit of the apparatus is shifted by the human interpupillary distance of a subject (the average human interpupillary distance is about 60 mm) in response to an input from a left-right changeover switch. Since the eye and the apparatus are, occasionally, not accurately aligned, a manual operation is further performed for alignment before pressing the measurement switch.

In the above conventional art, the operator is required to align further to some degree each time the apparatus is shifted from one to the other eye. When the operator is busy handling a plurality of optometric apparatuses at the same time, attending to the apparatus each time for the left-right switching is troublesome. When subjects themselves perform optometric measurement, they are required to move themselves so that their eyes fall within an alignment detection range when the shifting to the other eye is performed. A manual operation to put the apparatus to within an automatic alignment detection range needs a device such as a joystick or trackball.

SUMMARY OF THE INVENTION

It is an object of the present invention to provide an optometric apparatus which allows a subject himself or herself to operate the apparatus from an automatic alignment to a measurement in the measurement of the left and right eyes of the subject.

It is yet another object of the present invention to provide an optometric measurement method that allows the optometric measurement to be reliably shifted to the other eye subsequent to the measurement of one eye of the subject, by executing a program in the measurement of the left and right eyes of the subject.

According to one aspect of the present invention, the optometric apparatus includes luminous flux projecting means for projecting a luminous flux to an eye of a subject to be measured, imaging means for imaging an anterior part of the eye illuminated by the luminous flux projecting means, position detecting means for detecting the position of the eye in accordance with an image output from the imaging means, an optometric unit for measuring the eye, drive means for driving the optometric unit, and control means for controlling the drive means, wherein the control means controls the drive means to align the optometric unit with the eye in accordance with a signal output from the position detecting means and then controls the drive means to move the optometric unit to the other eye of the subject when the measurement of the eye by the optometric unit is completed.

According to another aspect of the present invention, the optometric apparatus includes an optometric unit for measuring an eye of a subject to be measured, drive means for driving the optometric unit, a start switch for generating a signal, control means, wherein the control means controls the drive means so that the optometric unit measures the eye after the drive means aligns the optometric unit with the eye in response to a signal from the start switch and then controls the drive means to move the optometric unit to the other eye of the subject subsequent to the completion of the measurement of the eye.

According to yet another aspect of the present invention, the optometric measurement method for automatically performing an optometric measurement in response to a signal from a start switch, includes the steps of aligning a measurement unit with one eye of a subject to be measured, of measuring the eye with the measurement unit, and of moving the measurement unit to the other eye of the subject.

According to yet another aspect of the present invention, the optometric apparatus includes luminous flux projecting means for projecting a luminous flux to an eye of a subject to be measured, imaging means for imaging an anterior part of the eye illuminated by the luminous flux projecting means, position detecting means for detecting the position of the eye in accordance with an image output from the imaging means, a measurement unit for measuring the eye, drive means for driving the measurement unit, and control means for controlling the drive means, wherein the control means controls the drive means in accordance with a signal output from the position detecting means that captures a wide area image, before controlling the drive means in accordance with a signal output from the position detecting means that captures a narrow area image.

BRIEF DESCRIPTION OF THE DRAWINGS

FIG. 10 is a circuit block diagram of a second embodiment of the present invention;

DESCRIPTION OF THE PREFERRED EMBODIMENTS

Figure 1:
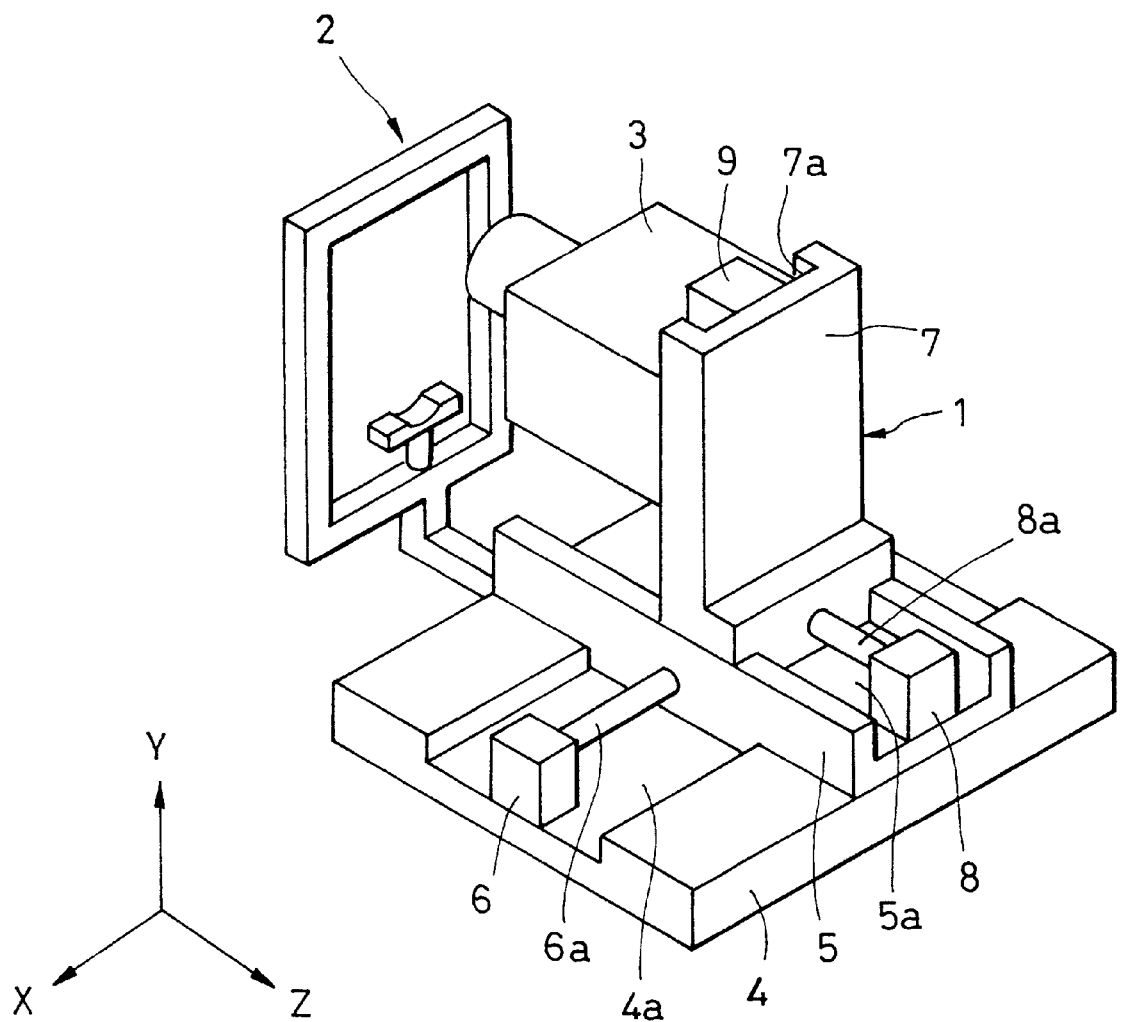
FIG. 1 is a perspective view showing a first embodiment of the optometric apparatus of the present invention.

Referring to the drawings, the embodiments of the present invention are now discussed.

FIG. 1 is a perspective view showing a first embodiment of optometric apparatus of the present invention. The optometric apparatus includes an apparatus body 1 and a face rest unit 2 on which the face of a subject is placed. The apparatus body 1 includes an optometric unit 3, and three stages for three-dimensionally moving the optometric unit 3. A support fixture 4, serving as a base, has a groove 4a extending in the direction of the X axis, and a movable unit 5 is seated in the groove 4a. A threaded rod 6a of a motor 6 attached to the support fixture 4 is mated with an internal thread portion formed in the movable unit 5. The movable unit 5 has a groove 5a extending in the direction of the Z axis, and a movable unit 7 is seated in the groove 5a. The movable unit 7 is mated with a threaded rod 8a of a motor 8 attached to the movable unit 5. The movable unit 7 has a groove 7a extending the direction of the Y axis (vertical direction), and the optometric unit 3 is seated in the groove 7a. The optometric unit 3 is mated with a threaded rod (not shown) of a motor 9 attached to the movable unit 7.

The motors 6, 8 and 9 are electrically connected to an unshown drive control circuit, thereby three-dimensionally driving the optometric unit 3 to a predetermined position. The motors 6, 8 and 9 may be any type motor such as a pulse motor or a DC motor. In a motor such as a DC motor in which the quantitative drive control is difficult, a sensor element for sensing the distance of travel of each stage or the angular travel of the motor is preferably arranged in the apparatus.

Figure 2:
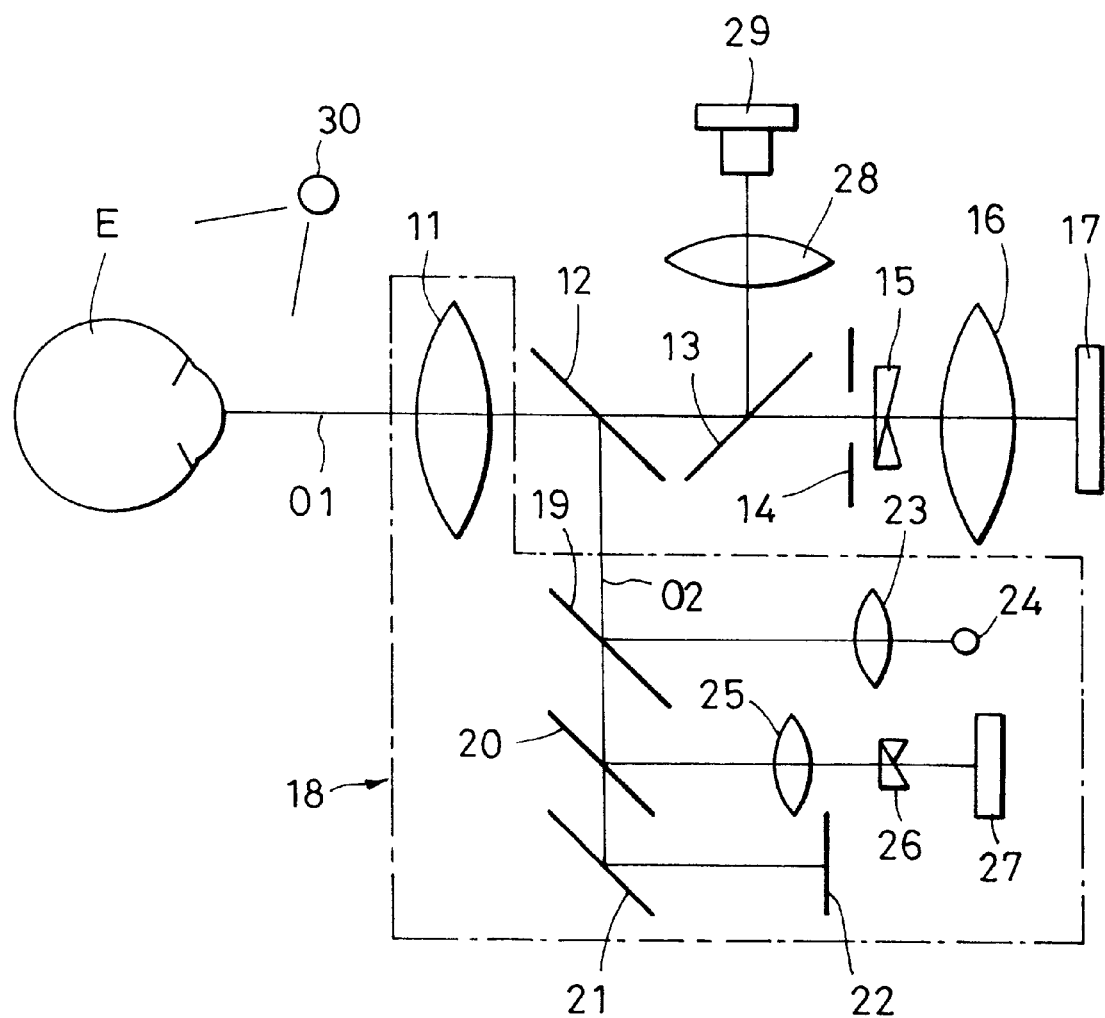
FIG. 2 is a block diagram showing an optical system of a refractometer section of the apparatus.
Figure 3:
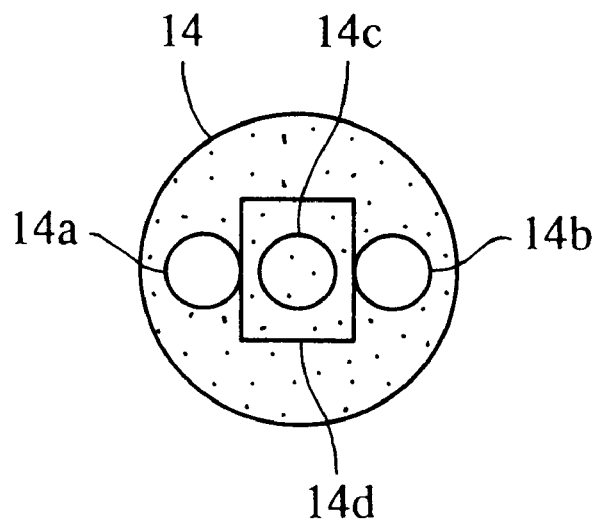
FIG. 3 is a front view of a mask.
Figure 4:
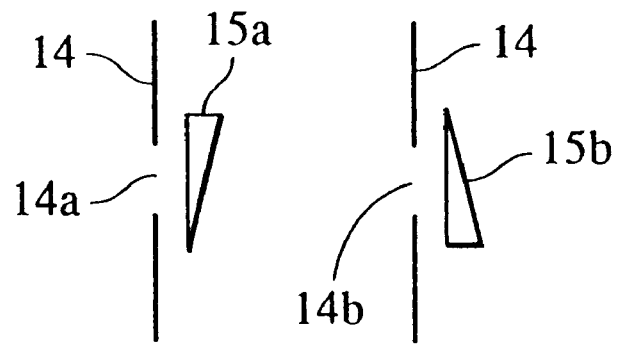
FIG. 4 is an explanatory diagram of a prism.

FIG. 2 shows an alignment optical system and a refractometric optical system of the optometric unit 3. Arranged in the optical path 01 extending toward the front of the eye E to be measured are an objective lens 11, dichroic mirrors 12 and 13, a mask 14 having three apertures 14a, 14b, and 14c as shown in FIG. 3, a prism set 15, including prisms 15a and 15b as shown in FIG. 4, on which is deposited a wavelength splitting film for transmitting the wavelength of an alignment light source to be described later, an imaging lens 16 and an imaging element 17.

Arranged in the direction of light reflected from the dichroic mirror 12 is a refractometric optical system 18 which includes, in the reflective optical path 02 of the dichroic mirror 12, dichroic mirrors 19 and 20, a mirror 21, and a fixation reticle 22. Arranged in the direction of light incident on the dichroic mirror 19 are a projection lens 23 and a measurement light source 24. An imaging lens 25, a six-segment prism 26, and an imaging element 27 are arranged in the direction of light reflected from the dichroic mirror 20. Arranged in the direction of light incident on the dichroic mirror 13 are a projection lens 28, and an alignment light source 29 including LEDs. An illumination light source 30 including LEDs is arranged slant to the front of the eye E.

In an alignment optical system, a luminous flux emitted from the alignment light source 29 is projected to the eye E via the projection lens 28, dichroic mirror 13, and objective lens 11. In an alignment receiving optical system, a luminous flux reflected from the eye E is transmitted through the objective lens 11, mask 14, prisms 15a and 15b, and is guided to the imaging element 17 via the imaging lens 16. The luminous flux transmitted through the apertures 14a and 14b of the mask 14 is refracted in upward and downward directions by prism set 15.

In an anterior part observation system, a luminous flux, emitted from the illumination light source 30, is reflected from the anterior part of the eye E, and is then guided to the imaging element 17 through the objective lens 11, the aperture 14c of the mask 14, and the imaging lens 16. A filter 14d, which transmits the waveform of the luminous flux from the illumination light source 30 only, covers the aperture 14c of the mask 14. The imaging element 17 is therefore shared by the alignment detection system and the anterior part observation system.

The luminous flux, emitted from the measurement light source 24, is guided to the eye E via the projection lens 23, dichroic mirror 19, dichroic mirror 12, and objective lens 11. The luminous flux, reflected from the eye-ground, reverses the same path to the dichroic mirror 19. The reflected luminous flux is transmitted through the dichroic mirror 19, reflected off the dichroic mirror 20, passed through the imaging lens 25, split through the six-segment prism 26, and guided to the imaging element 27.

The above optical systems are divided into an alignment detection optical system and a refractometric optical system 18. A tonometric optical system may be substituted for the refractometric optical system 18. In an embodiment shown in FIG. 5, the refractometric optical system 18 is replaced with the tonometric optical system 31. A nozzle 33 is arranged in the center of an objective lens 32, and a compressor chamber 34, through which an observation window along the optical path 01 extends, is arranged behind the objective lens 32. A piston 35 is movably mounted in the compressor chamber 34. The piston 35 is driven by a rotary solenoid 36.

Figure 5:
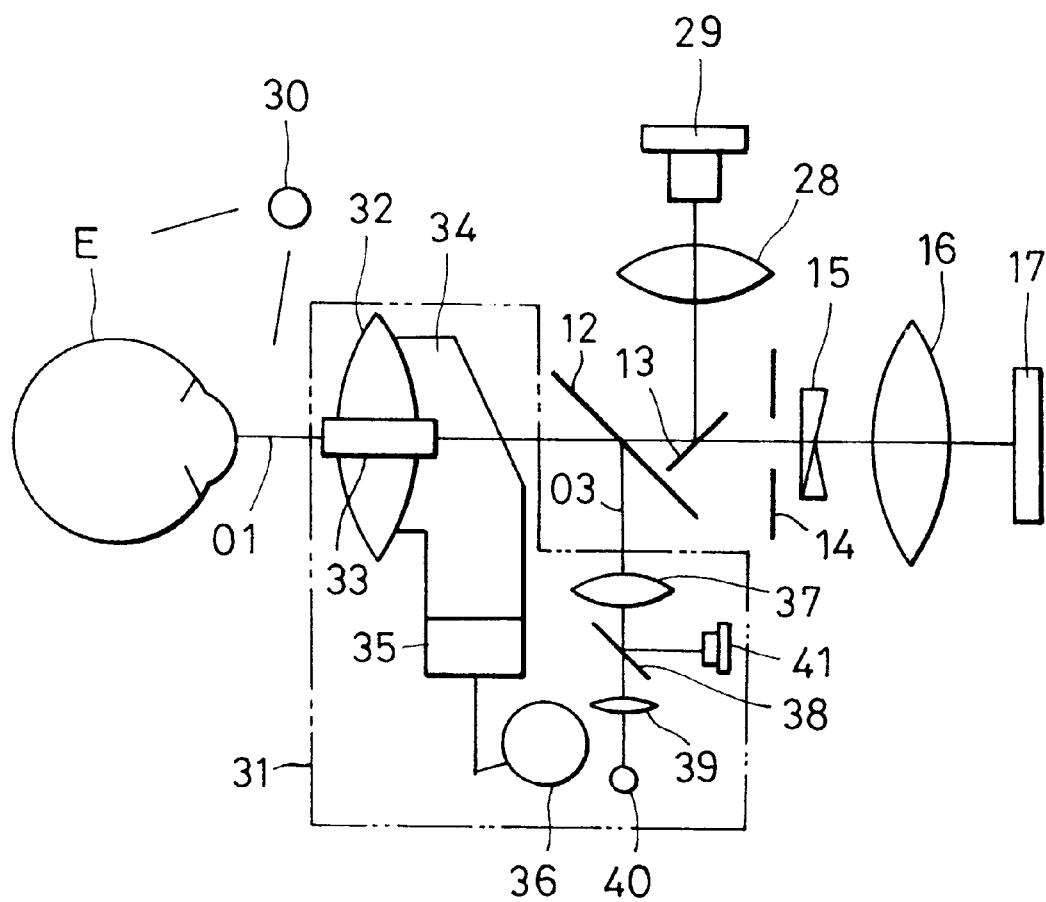
FIG. 5 is a block diagram showing an optical system of a tonometer section of the apparatus.

Arranged in an optical path 03 in the direction of light incident on the dichroic mirror 12 are a lens 37, a half mirror 38, lens 39, light source 40, and photoreceptor element 41 are arranged in the direction of light reflected from the half mirror 38. In FIG. 5, components identical to those described with reference to those shown in FIG. 2 are designated with the same reference numerals.

The piston 35, driven by the rotary solenoid 36, moves and ejects air through the nozzle 33 toward the eye E. The luminous flux from the light source 40 irradiates the cornea of the eye E through the lenses 39 and 37 and the nozzle 33. The luminous flux, reflected from the eye E, returns to the half mirror 38 via the objective lens 32 and lens 37 and reaches the photoreceptor element 41. In this way, the photoreceptor element 41 receives a maximum quantity of light when the cornea of the eye E is deformed in a predetermined shape in response to the impinging air.

Figure 6A:
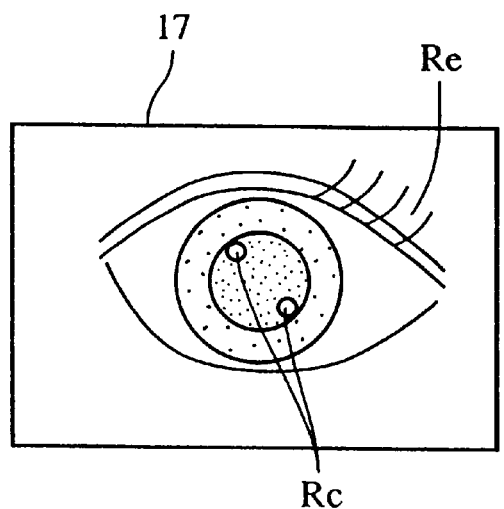
FIG. 6A through FIG. 6C are explanatory diagrams of an observed image.
Figure 6B:
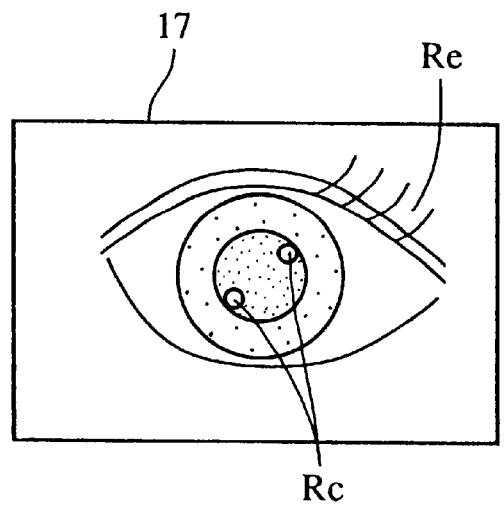
Figure 6C:
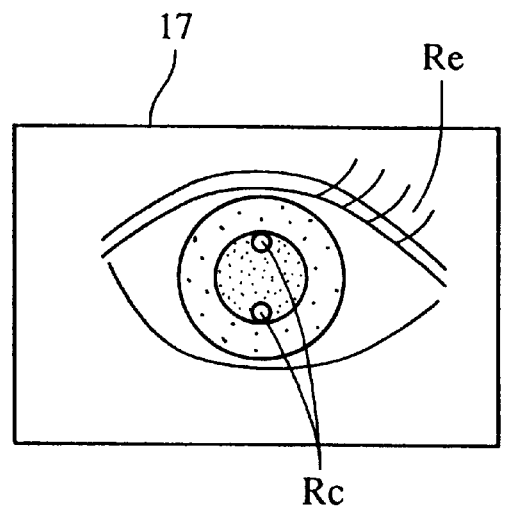

In the optometric apparatuses having optical systems shown in FIG. 2 and FIG. 5, the anterior part of the eye is imaged on the imaging element 17 as shown in FIGS. 6A through 6C when the apparatus is adjusted to align with eye E. The image Re of the eye E and corneal reflex images Rc in response to the light from the alignment light source 29 are superimposed on screen. Corneal reflex images Rc, which consist of two bright spots from the apertures 14a and 14b of the mask 14 are shifted from predetermined positions in the X and Y directions in the field of view of the imaging element 17, depending on the position of the eye E. The error in the Z direction is determined by the errors of the two bright spots in the X direction as shown in FIG. 6A and FIG. 6B. When the eye is placed in an appropriate position in the X, Y, and Z directions as shown in FIG. 6C, refractometry and tonometry are started.

Figure 7:
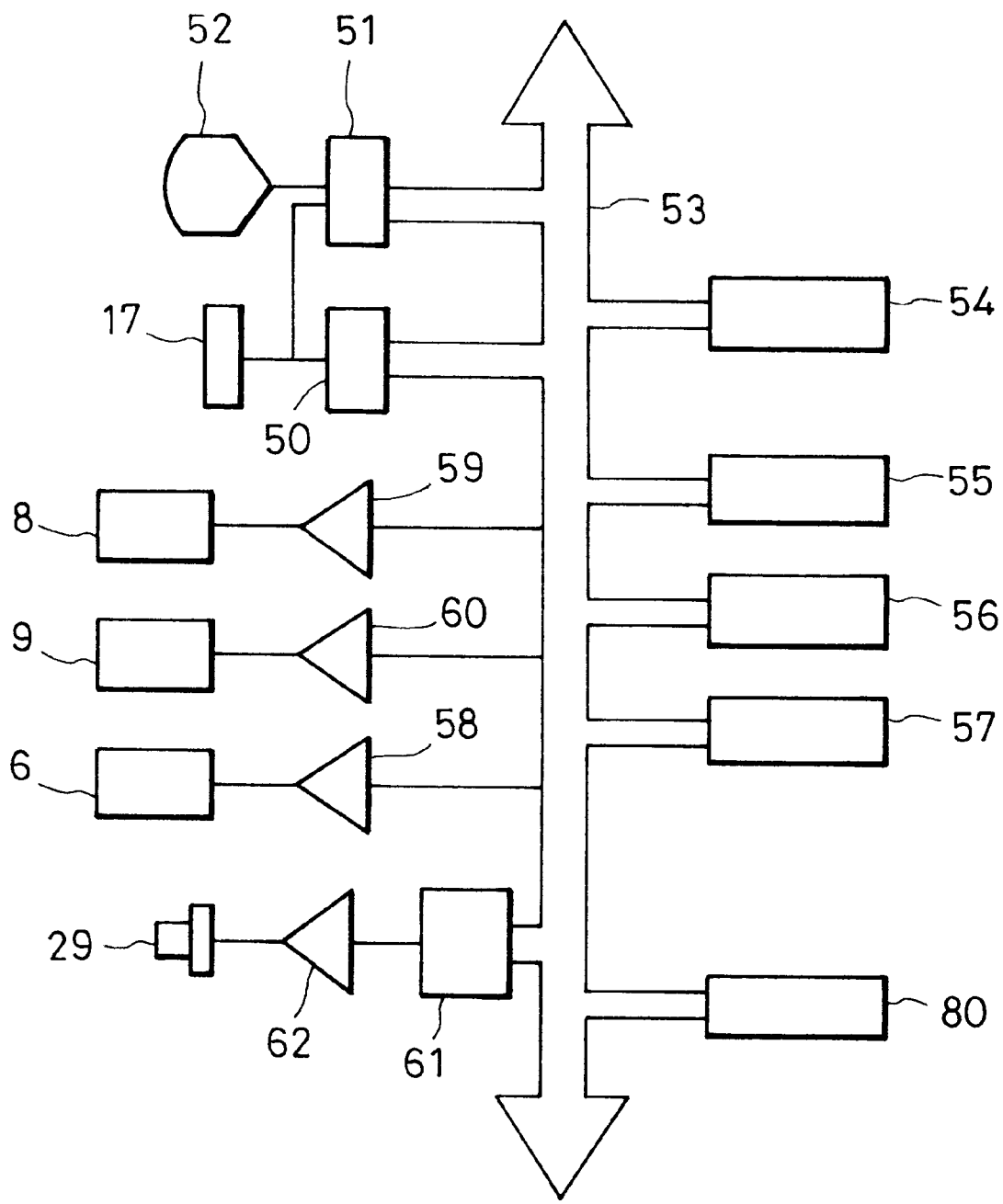
FIG. 7 is an electrical circuit diagram of the apparatus.

FIG. 7 is an electrical circuit block diagram of the optometric apparatus. The output of the imaging element 17 is coupled to an A/D converter 50 and an image synthesis circuit 51. The outputs of these circuits are fed to a display 52 and a data bus 53. The output of the A/D converter 50 is fed to a video memory 54, CPU 55, ROM 56, and RAM 57 via the data bus 53. Signals from CPU 55 are supplied to drivers 58, 59, and 60, which respectively drive motors 6, 8 and 9 for moving the respective stages, and to a D/A converter 61 and a driver 62 for driving the alignment light source 29. A start switch 80 is used to start an automatic alignment operation and optometrical measurement. The data bus 53 is connected to other various devices required for the optometric measurement.

Figure 8:
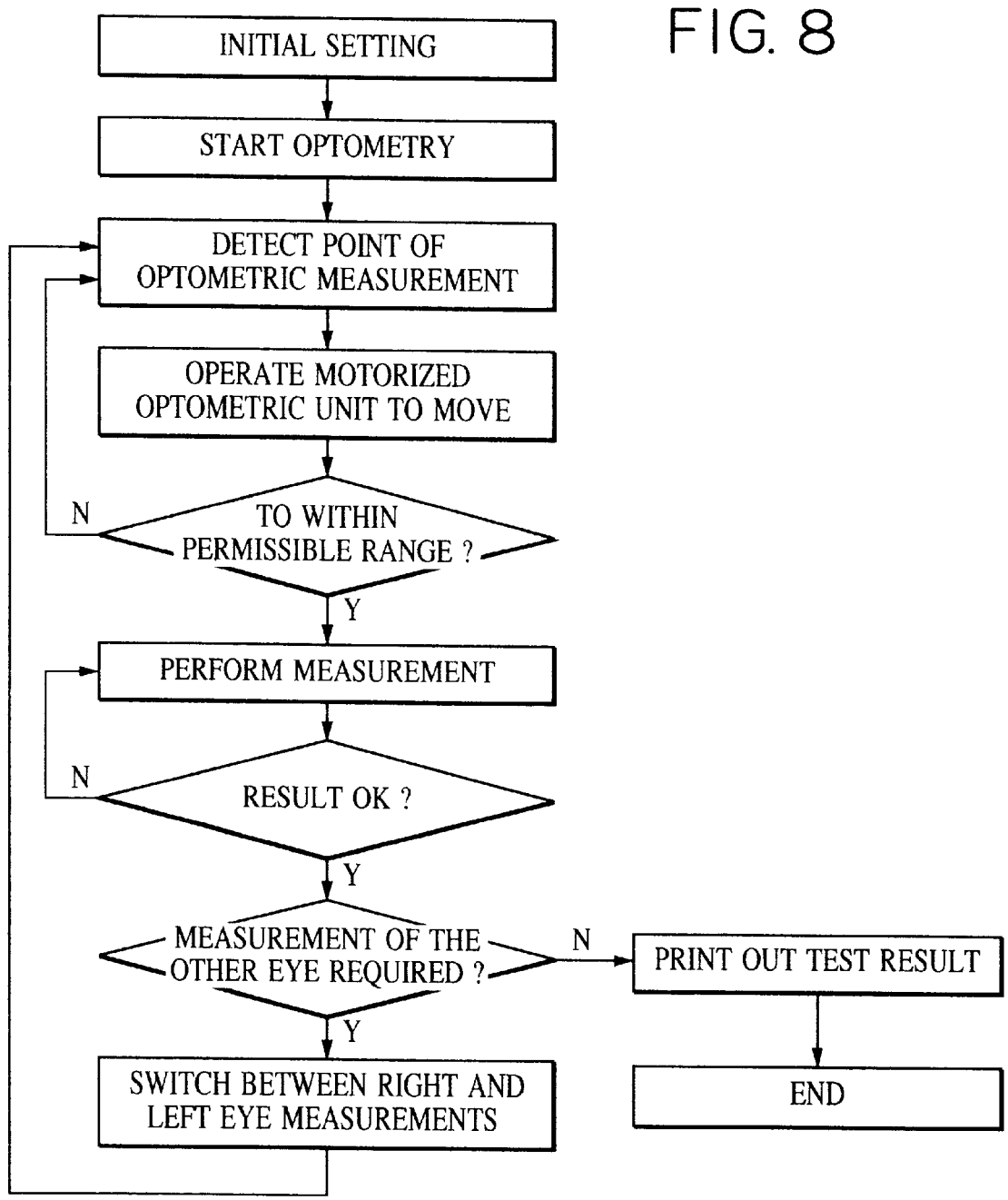
FIG. 8 is a flow diagram of an optometric measurement of the apparatus.

FIG. 8 is a flow diagram of the optometric measurement. When an operator turns on a power switch, the devices are automatically initialized and a program stored in ROM 56 is automatically loaded. The operator performs an initial setting. For example, the operator enters an ID number and information such as "one-eye-only" measurement, and sets the face rest unit. To roughly align the optometric unit 3 with the eye, the operator manipulates an unshown track ball and alignment switches while watching the display 52, thereby drives the motors 6, 8 and 9 in three directions. Subsequent to the initial setting, the operator presses the start switch 80, thereby causing the apparatus to start the alignment and optometric measurement.

When the optometric measurement starts, the optometric apparatus operates and processes signals in accordance with commands from CPU 55. Activated by the measurement start, the alignment light source 29 is lit, and the measurement light source 24 is lit, and then the alignment detection process is performed.

The anterior part of the eye E is imaged on the imaging element 17, and the corneal reflex images Rc are presented as shown in FIG. 6A through FIG. 6B. As already discussed, a misalignment between the eye E being measured and the optometric unit 3 in the X, Y, and Z directions is corrected. Specifically, part of the image obtained in the imaging element 17 is fed to the image synthesis circuit 51, and the remaining image is A/D-converted by the A/D converter 50, and stored in the video memory 54. CPU 55 processes the data stored in the video memory 54 to extract two bright spots of the corneal reflex images, calculates the coordinates of the center of each bright spot, and then a deviation to the appropriate position. How far the optometric unit 3 needs to travel in the X, Y and Z directions is then computed. Drive commands are then output to the motors 6, 8 and 9. When the eye E fails to fall within a permissible range in a single trial, for example, due to a slight vibration, the image capturing is made again, and position detection is performed again.

When repetitions of such a feedback control put the misalignment to within a permissible range, the optometric measurement is started. In the refractometry measurement, the luminous flux from the measurement light source 24 is reflected from the eye-ground, and is received, as a six-spot image, by the imaging element 27 while the fixation reticle 22 is moved. A refractive power is thus computed from the received six-spot image. The final refractive power is determined when the subject recognizes the fixation reticle 22 as a foggy one. In the tonometry measurement, the rotary solenoid 36 is operated, ejecting air to the eye E. The ocular tension of the eye E is computed, based on the internal pressure in the compressor chamber 34 when the cornea deforms in the predetermined shape, causing the photoreceptor 41 to give a maximum output. The time required from the alignment to the optometric measurement is preferably within several seconds to lighten the burden on the subject.

CPU 55 determines whether the optometric measurement is successful. More specifically, CPU 55 determines whether the measurement signal is obtained or reaches a predetermined level. When the optometric measurement is not successful, CPU 55 returns to the alignment operation with the eye being measured. When the optometric measurement is successful, CPU 55 stores in RAM 57 a flag indicating that one eye measurement is complete, and sends a measurement result to the image synthesis circuit 51 for display on the display 52. The apparatus is then shifted to the other eye. When the "one-eye-only" measurement is set in the initial setting, the measurement result is printed out and the optometric measurement ends.

When a "both-eye" measurement is set, the motors 6, 8 and 9 move the optometric unit 3 to the other eye by a predetermined distance corresponding to the interpupillary distance of the subject (the average human interpupillary distance is about 60 mm). A predetermined distance for children only or any particular group only may be selected in the initial setting if their interpupillary distances fall within a relatively narrow range. Alternatively, the distance to travel may be set to the interpupillary distance computed from the left eye position and the right eye position of the eyes actually measured. The movement to the other eye may be initiated in response to a measurement end signal or a display end signal of the preceding measurement. In the operation of the movement of the optometric unit 3 to the other eye, the capturing of the corneal reflex image Rc of the other eye starts at the moment when the optometric unit 3 reaches half the distance of travel. When CPU 55 extracts an area having a large light quantity from the data stored in the video memory 54, like a bright spot, the alignment light source 29 is extinguished, and the image capturing begins again.

Figure 9A:
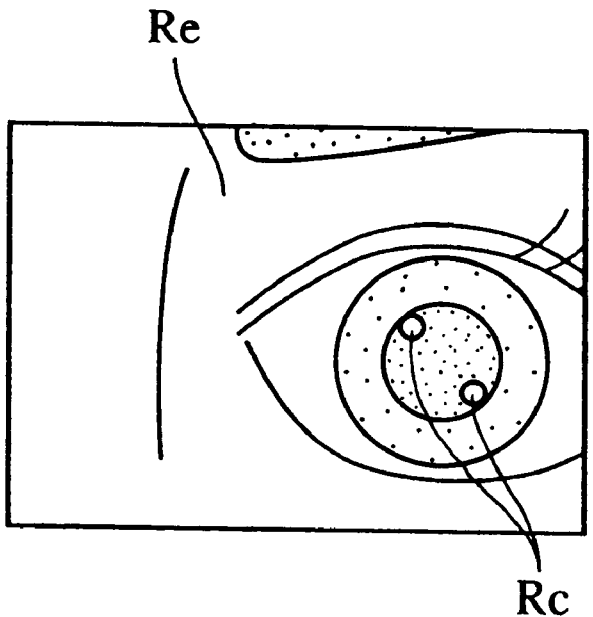
FIG. 9A and FIG. 9B are explanatory diagrams of an observed image when the apparatus is switched for the optometric measurement between the left and right eyes of a subject.
Figure 9B:
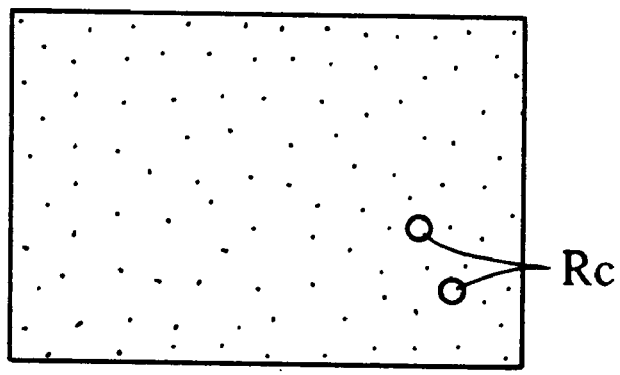

The video data of the two images are differentially processed to exclude external noise, and to extract the corneal reflex image Rc only. Although a slight time delay occurs between the two captured images, a deviation due to the time delay is corrected referring to the speed and direction of the optometric unit 3, and the two images are thus subjected to the differential process. FIG. 9A shows an image that is captured in the middle of movement. FIG. 9B shows a differential-processed image. The center of each of the two bright spots of the corneal reflex images Rc extracted is computed. The center-to-center distance between the two bright spots is also computed. When the center-to-center distance of the two bright spots is equal to the distance of the corneal reflex images that are beforehand formed, the corneal reflex images Rc are verified as true ones.

When the corneal reflex images Rc are recognized in the middle of the movement of the optometric unit 3 to the other eye E, the position detection process to the other eye E is directly entered. In the same manner as in the eye E previously measured, the optometric unit 3 is aligned with the other eye E to within a permissible range with the motors 6, 8 and 9. The refractometry and the tonometry are then automatically carried out.

When the optometric measurement is successful, the measurement result is sent to the image synthesis circuit 51 to display it on the display 52. The measurement result of the other eye, stored in RAM 57, is printed out on an unshown printer. The interpupillary distance is computed from the left and right eye positions in response to the clearance of the measurement end flags of both eyes, and the past interpupillary distance data is averaged. The measurement light source 24 and the alignment light source 29 are extinguished. The measurement result, synthesized through the image synthesis circuit 51 and presented on the display 52, is cleared. The optometric measurement is thus completed.

In the above embodiment, the measurement result is picked up once. In the tonometry in which a plurality of measurements are performed to obtain a reliable measurement value, a serial measurement mode is beforehand incorporated in a program, and is selected in the initial setting. In such a case, the alignment operation and the determination of the optometric measurement result are repeated by a predetermined number of times, for example, three times, and the other eye is measured. The same loop is repeated in the other eye. When both eyes are measured, the optometric measurement is completed.

In the above embodiment, the results are printed out subsequent to the optometric measurement of both eyes. Instead of the printing of the measurement result, the data may be transferred to a computer or the like, or is printed out while being transferred to a computer or the like at the same time. The optometric apparatus of the present invention thus does not require operator's intervention from the start of the optometric measurement to the end of the measurement of both eyes. The operation of the apparatus is thus simple.

FIG. 10 is a block diagram of a second embodiment of the present invention, showing blocks added to the data bus 53 shown in FIG. 7. In second embodiment, the start switch 80 is operated by the subjects themselves. A face sensor switch 71 is connected to the data bus 53 via the A/D converter 70. The face sensor switch 71 is a touch microswitch, mounted on the jaw rest portion of the face rest unit 2 shown in FIG. 1. The face sensor switch 71 is turned on when the subject places his or her face on the rest unit 2. A signal generated in response is sent to CPU 55 via the A/D converter 70. The flag indicative of the subject's face placement is set in RAM 57, and is reset when the face sensor switch 71 is turned off.

Figure 11:
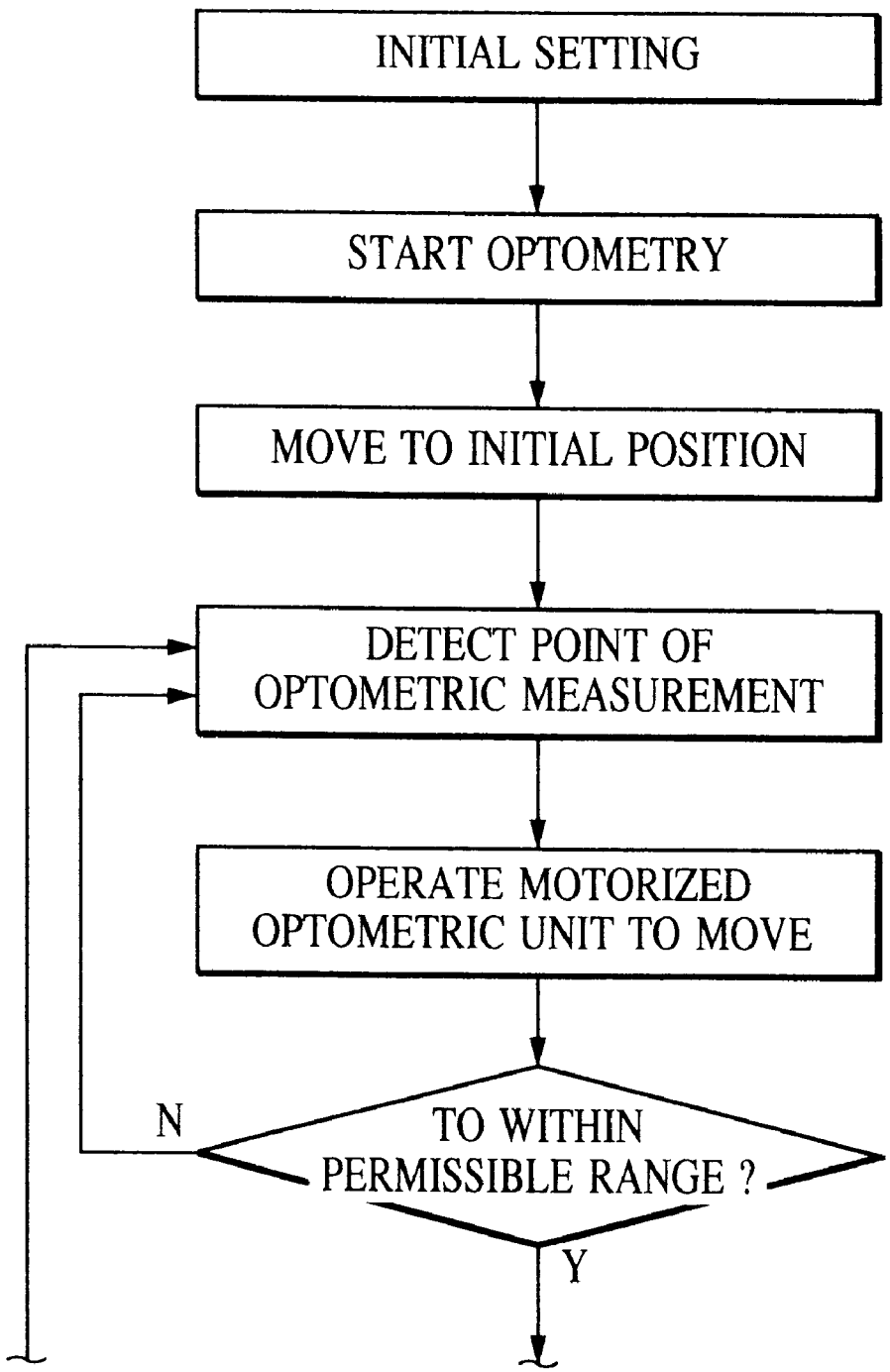
FIG. 11 is a flow diagram of the optometric measurement in the second embodiment.

FIG. 11 is a flow diagram showing the optometric measurement, in which a modification is included in the preceding embodiment and the unshown portion thereof remains unchanged. The modified portion is included in a program and is stored in ROM 56.

When the subject switches on the apparatus, the program in ROM 56 is automatically loaded. When the subject places his or her face on the face rest unit 2, the face sensor switch 71 is turned on, and the optometric measurement start switch is thus turned on. In response to the start switch being turned on, the optometric unit 3 is automatically shifted to a predetermined position, namely, an initial position that is aligned with the left eye or right eye which is expected to be in the face rest unit 2. Along with this movement, the image capturing is performed so as to detect the corneal reflex images Rc.

When the eye E is recognized in the same manner as in the preceding embodiment, the deviation of the optometric unit 3 from the appropriate position is computed. The motors 6, 8 and 9 run to make the optometric unit 3 align with the eye E to within a permissible range. The optometric measurement, such as the refractometry and the tonometry, is automatically performed. The measurement of the other eye and output of the measurement results are carried out in the same manner as in the preceding embodiment. The apparatus is thus easy to use. The operator performs the optometric measurement, by simply operating the measurement start switch. The system is simple and less costly, because the track ball and alignment switch for a rough alignment are removed from the system.

The face sensor switch 71 mounted on the face rest unit 2 may be constructed of a transmissive type infrared sensor assembly installed on both poles that come to the sides of the face when the subject's face is placed on the face rest unit 2.

In the above discussion, the eye position is detected by capturing the corneal reflex images Rc. The illumination light source 30 is lit brightly at the same moment when the image is captured, and a dark circular area corresponding to the pupil is detected from the captured data. The dark area is regarded as the pupil of the eye E being measured, and the position of the eye being measured is thus detected. Depending on the design of the optical systems, the dark area is detected from a wider area than the corneal reflex image. This precludes a situation under which the optometric measurement is unsuccessful for a long time because of a failure to detect the eye E. To precisely perform the alignment, the position detection of the corneal reflex image Rc is also performed so that the alignment is performed in a wide area.

The above system is used as an optometric apparatus operated by the subjects themselves. The predetermined position set in response to the input from the optometric measurement start switch may be set to the position of the right eye or the left eye in the initial setting, depending on the installation condition of the apparatus. For example, when the apparatus on the left eye side faces the wall of a room, the eye E and the optometric unit 3 are more easily measured in height on the right eye side and the jaw rest portion of the face rest unit 2 is easy to measure in height. When the apparatus on the right eye side faces the wall of a room, the above setting is reversed.

Figure 12:
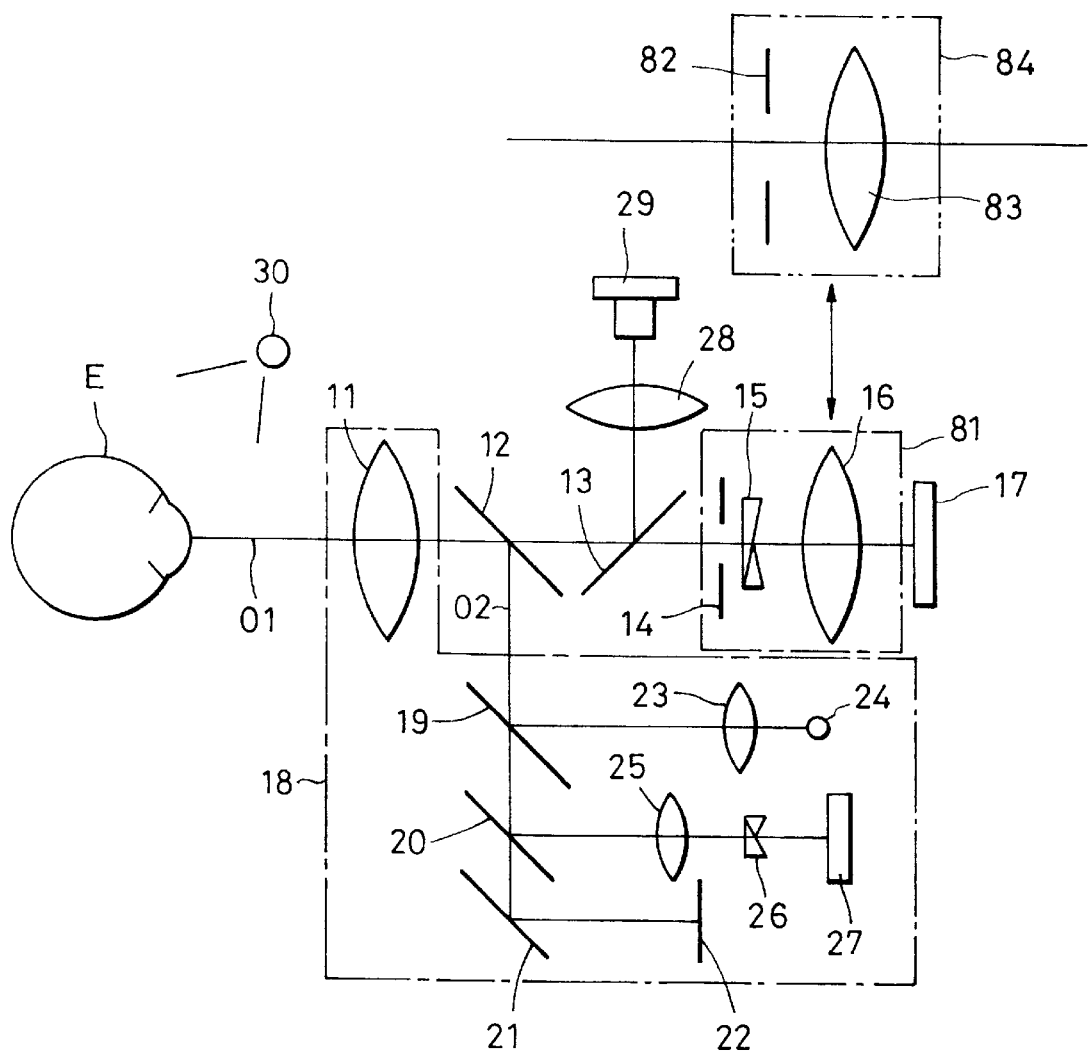
FIG. 12 is a block diagram showing the optical system of a refractometer in accordance with a third embodiment of the present invention.

FIG. 12 shows a third embodiment of the present invention. Components identical to those described with reference to FIG. 2 are designated with the same reference numerals. A magnifying lens unit 81 composed of a mask 14, a prism 15 and an imaging lens 16 is interchangeable with a reduction lens unit 84 composed of an aperture plate 82 and a reduction lens 83.

Figure 13:
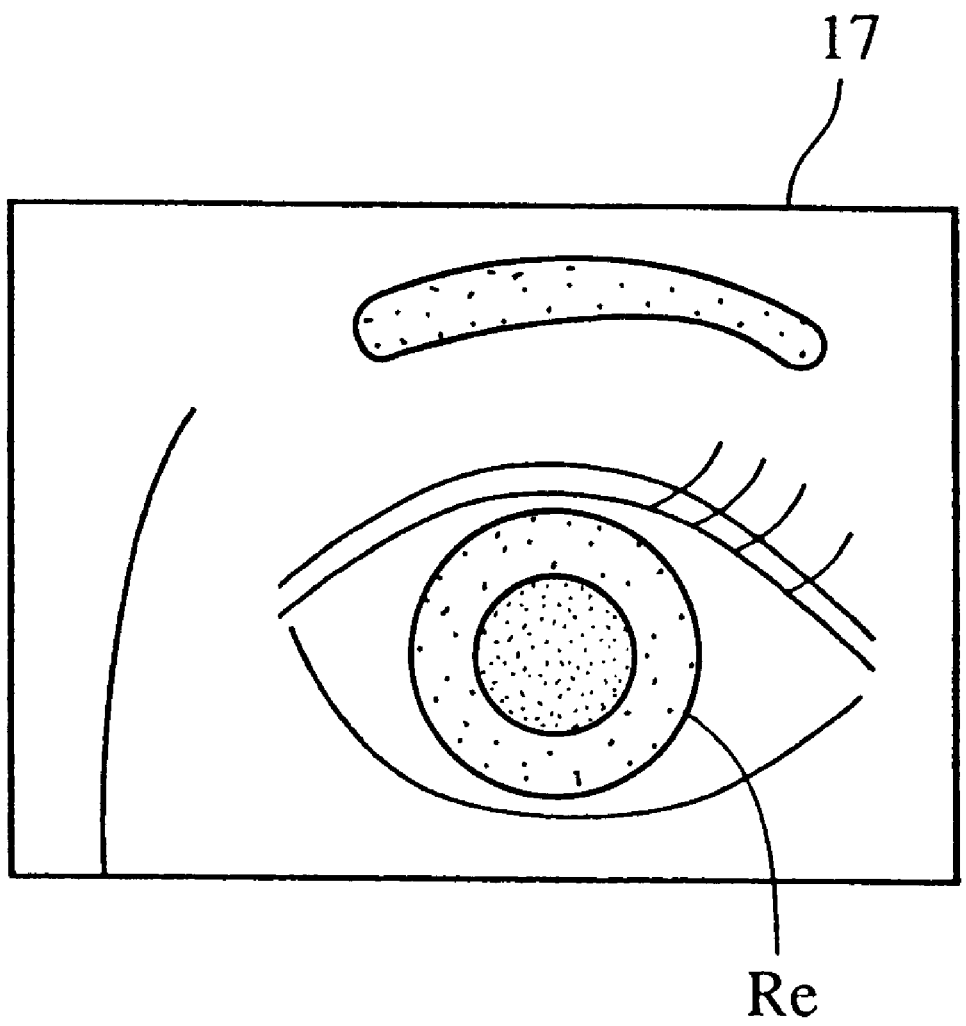
FIG. 13 is an explanatory view of an observed image.

The magnification of the system is changed when the lens units 81 and 84 are interchanged through an electrical control by means of a motor or solenoid. When the reduction lens unit 84 is used, the image Re of the eye E being measured is observed in a reduced scale as shown in FIG. 13. The aperture plate 82 increases the depth of field, permitting the operator to observe the eye E being measured in a wide area.

Figure 14:
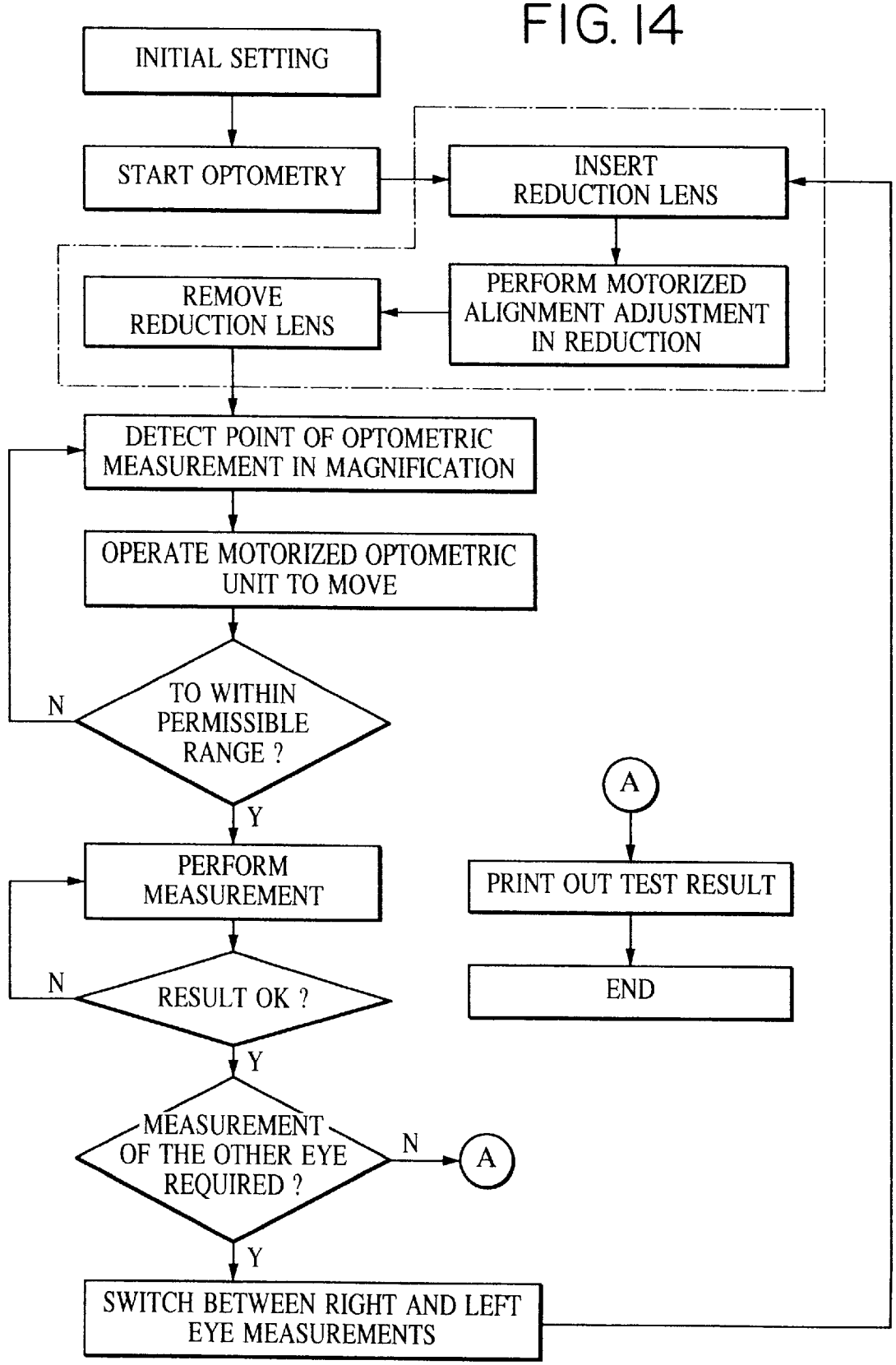
FIG. 14 is a flow diagram of the optometric measurement in the embodiment.

FIG. 14 is a flow diagram showing the measurement operation by the above system. Blocks surrounded by a dotted line change the optical magnification. When the initial setting is made, as in the preceding embodiment, the optometric measurement start switch demounts the magnifying lens unit 81, and mounts the reduction lens unit 84. The observed image through the reduction lens unit 84 is shown in FIG. 13. The deviation of the optometric unit 3 is detected by the method of detecting the pupil of the eye E being measured.

Since the pupil detection is performed in a reduced scale in this case, the detection area of the pupil becomes even wider. The deviation of the optometric unit 3 is converted into the distance of travel, and the drivers are controlled to move the optometric unit 3 to within a permissible range in a reduced scale, thereby performing the alignment operation. When the optometric unit 3 comes into the permissible range, the reduction lens unit 84 is demounted, and the magnifying lens unit 81 is mounted. The alignment light source is lit at the moment the magnifying lens 81 is mounted. In accordance with the corneal reflex images, a fine alignment operation is carried out.

When the optometric unit 3 is placed to the appropriate position, the optometric measurement is performed. When the optometric measurement is successful, the left-right switching operation is carried out for the measurement of the other eye. At the same time the magnifying lens unit 81 is automatically demounted, and the reduction lens unit 84 is automatically mounted. A coarse alignment operation at the reduced scale and then a fine alignment operation at the magnified scale are performed to measure the other eye.

Since a wide area of the eye E is observed through the observation and position detection from the reduced scale to the magnified scale, simply touching the optometric measurement switch, automatically, aligns the optometric unit 3 with the eye E, performs the optometric measurement, switches between the left and right eyes, and prints out the measurement results. The ease of use of the apparatus is substantially promoted.

Figure 15:
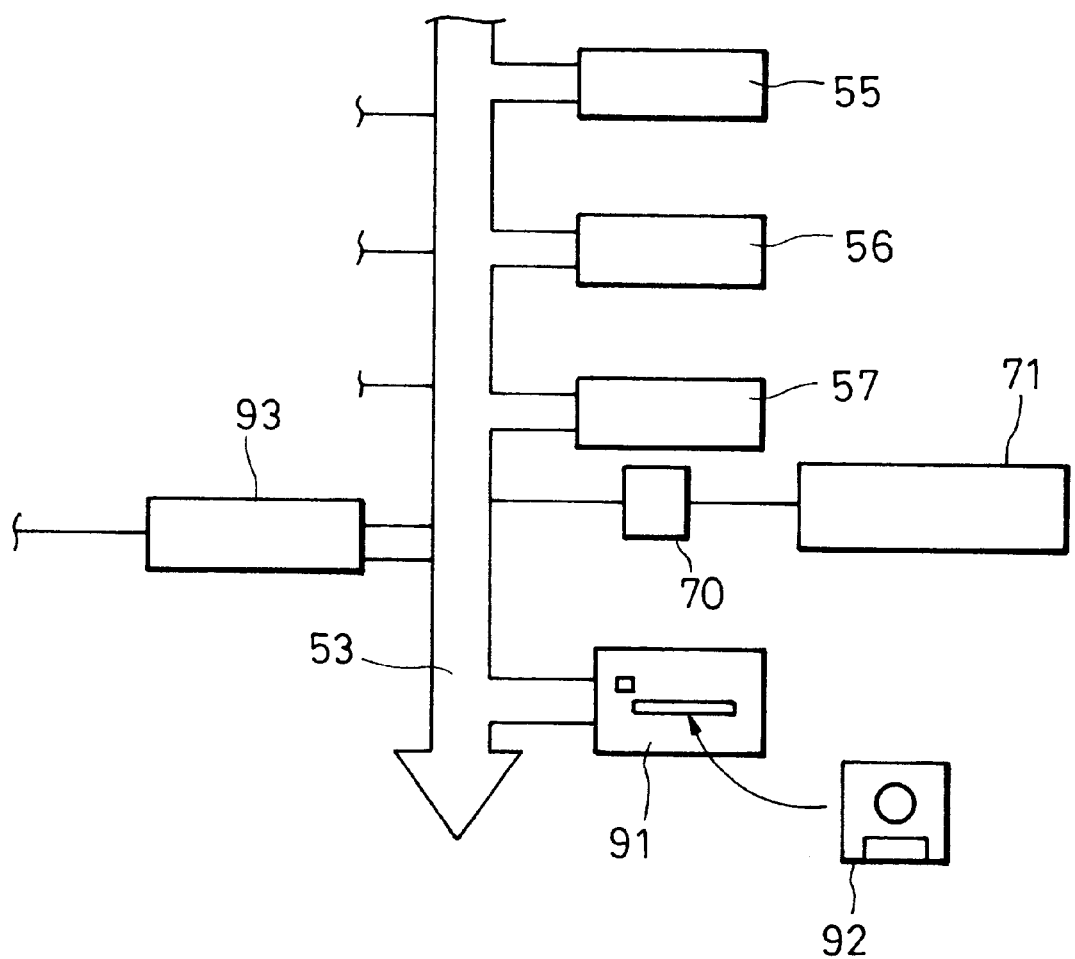
FIG. 15 is a circuit block diagram of an alternate embodiment of the present invention.

FIG. 15 is a block diagram of the system in which the control program stored in ROM 56 is stored in a storage medium such as a floppy disk to use the alignment control in another optometric apparatus. A disk drive 91 is connected to the data bus 53, and the storage medium 92 is loaded thereto and unloaded therefrom. A modem 93 is also connected to the data bus 53. A host computer connected through a network may load the control program.

A plurality of control programs having different initial settings are prepared so that an operator may select one matching an optometric apparatus in use or a subject of interest. Furthermore, the control program is associated with a voice guide program under which a subject can follow a voice instruction for the measurement or a display screen control program. With this arrangement, the optometric apparatus becomes a subject-operated version.

The optometric apparatus of the present invention needs no operator's intervention to switch between the left eye and right eye, and automatically performs the optometric measurement from the alignment operation to the end of the actual measurement.

The optometric measurement method of the present invention allows the optometric measurement to be reliably shifted to the other eye subsequent to the measurement of one eye of the subject, by executing a program in the measurement of the left and right eyes of the subject.

While the present invention has been described with respect to what is presently considered to be the preferred embodiments, it is to be understood that the invention is not limited to the disclosed embodiments. The present invention is intended to cover various modifications and equivalent arrangements included within the spirit and scope of the appended claims.

What is claimed is:

1. An optometric apparatus comprising:

luminous flux projecting means for projecting a luminous flux to one eye of a subject to be measured;

imaging means for imaging an anterior part of said one eye illuminated by said luminous flux projecting means;

position detecting means for detecting the position of said one eye in accordance with an image output from said imaging means;

an optometric unit for measuring said one eye;

drive means for driving said optometric unit; and control means for controlling said drive means, wherein said control means controls said drive means to align said optometric unit with said one eye in accordance with a signal output from said position detecting means and then controls said drive means to move said optometric unit to the other eye of said subject when the measurement of said one eye by said optometric unit is completed.

2. An optometric apparatus according to claim 1, wherein said control means controls said drive means to three-dimensionally move said optometric unit in accordance with the signal output from said position detecting means.

3. An optometric apparatus according to claim 1, wherein said control means controls said drive means to move said optometric unit to an initial position prior to controlling said drive means in accordance with the signal output from said position detecting means.

4. An optometric apparatus according to claim 3, further comprising sensing means for sensing the proximity or touch of the face of said subject to said optometric apparatus, wherein said control means controls said drive means to move said optometric unit to said initial position in accordance with a sensed signal of said sensing means.

5. An optometric apparatus according to claim 1, wherein said position detecting means detects the position of a corneal reflex image of said one eye in response to the luminous flux projected by said luminous flux projecting means.

6. An optometric apparatus according to claim 1, wherein said optometric unit measures a refractive power of said one eye.

7. An optometric apparatus according to claim 1, wherein said optometric unit measures an ocular tension of said one eye.

8. An optometric apparatus comprising:

an optometric unit for measuring one eye of a subject to be measured;

drive means for driving said optometric unit;

a start switch for generating a signal; and control means, wherein said control means controls said drive means so that said optometric unit measures said one eye after said drive means aligns said optometric unit with said one eye in response to said signal from said start switch and then controls said drive means to move said optometric unit to the other eye of said subject subsequent to the completion of the measurement of said one eye.

9. An optometric measurement method for automatically performing an optometric measurement in response to a signal from a start switch, said method comprising the steps of:

aligning a measurement unit with one eye of a subject to be measured;

measuring said one eye with said measurement unit; and moving said measurement unit to the other eye of said subject.

10. An optometric measurement method according to claim 9, further comprising a step of displaying the measurement result of said measuring step.

11. An optometric measurement method according to claim 9, wherein said measuring step is repeated for a plurality of times.

12. An optometric measurement method according to claim 9, further comprising a step of aligning said measurement unit with said other eye of said subject subsequent to said moving step.

13. An optometric measurement method according to claim 9, further comprising a step of measuring said other eye with said measurement unit.

14. A machine readable medium for storing a program, said program comprising the steps of:

aligning a measurement unit with one eye of a subject to be measured;

measuring said one eye with said measurement unit; and moving said measurement unit to the other eye of said subject.

15. A machine readable medium for storing a program, said program comprising the steps of:

aligning a measurement unit with one eye of a subject to be measured;

measuring said one eye with said measurement unit;

moving said measurement unit to the other eye of said subject; and displaying the measurement result of said measuring step.

16. An optometric apparatus comprising:

luminous flux projecting means for projecting a luminous flux to one eye of a subject to be measured;

imaging means for imaging an anterior part of said one eye illuminated by said luminous flux projecting means;

position detecting means for detecting the position of said one eye in accordance with an image output from said imaging means;

a measurement unit for measuring said one eye;

drive means for driving said measurement unit; and control means for controlling said drive means, wherein said control means controls said drive means in accordance with a signal output from said position detecting means that captures a wide area image, before controlling said drive means in accordance with a signal output from said position detecting means that captures a narrow area image.

* * * * *